US008679481B2

(12) United States Patent
Gruskin et al.

(10) Patent No.: US 8,679,481 B2
(45) Date of Patent: Mar. 25, 2014

(54) METHODS OF REDUCING EXTRAVASATION OF INFLAMMATORY CELLS

(75) Inventors: Elliott A. Gruskin, Killingworth, CT (US); Jack L. Tseng, Stormville, NY (US); Anthony O. Caggiano, Larchmont, NY (US)

(73) Assignee: Acorda Therapeutics, Inc., Ardsley, NY (US)

( * ) Notice: Subject to any disclaimer, the term of this patent is extended or adjusted under 35 U.S.C. 154(b) by 245 days.

(21) Appl. No.: 13/103,347

(22) Filed: May 9, 2011

(65) Prior Publication Data

US 2011/0262413 A1 Oct. 27, 2011

Related U.S. Application Data

(62) Division of application No. 10/847,636, filed on May 17, 2004, now Pat. No. 7,959,914.

(60) Provisional application No. 60/471,189, filed on May 16, 2003.

(51) Int. Cl.
*A61K 38/43* (2006.01)
*A61K 38/51* (2006.01)

(52) U.S. Cl.
USPC ....... 424/94.61; 424/94.5; 424/94.1; 435/232

(58) Field of Classification Search
USPC ..................... 424/94.61, 94.1, 94.5; 435/232
See application file for complete search history.

(56) References Cited

U.S. PATENT DOCUMENTS

| | | | |
|---|---|---|---|
| 5,262,522 A | 11/1993 | Gearing | |
| 5,270,194 A | 12/1993 | D'Alterio et al. | |
| 5,496,718 A | 3/1996 | Hashimoto | |
| 5,498,536 A | 3/1996 | Khandke | |
| 5,578,480 A | 11/1996 | Khandke | |
| 5,652,122 A | 7/1997 | Frankel et al. | |
| 5,670,617 A | 9/1997 | Frankel et al. | |
| 5,674,980 A | 10/1997 | Frankel et al. | |
| 5,747,641 A | 5/1998 | Frankel et al. | |
| 5,763,205 A | 6/1998 | Hashimoto et al. | |
| 5,792,743 A | 8/1998 | Schachner | |
| 5,804,604 A | 9/1998 | Frankel et al. | |
| 5,869,301 A | 2/1999 | Nghiem et al. | |
| 5,997,863 A | 12/1999 | Zimmermann et al. | |
| 6,007,810 A | 12/1999 | Ishikawa et al. | |
| 6,063,378 A | 5/2000 | Nohara et al. | |
| 6,093,563 A | 7/2000 | Bennett et al. | |
| 6,153,187 A | 11/2000 | Yacoby-Zeevi | |
| 6,171,575 B1 | 1/2001 | Okuyama | |
| 6,184,023 B1 | 2/2001 | Hashimoto et al. | |
| 6,200,564 B1 | 3/2001 | Lamont et al. | |
| 6,248,562 B1 | 6/2001 | Dunn et al. | |
| 6,313,265 B1 | 11/2001 | Phillips et al. | |
| 6,326,166 B1 | 12/2001 | Pomerantz et al. | |
| 6,972,168 B2 | 12/2005 | Muir | |
| 7,008,783 B1 | 3/2006 | Sato et al. | |
| 7,074,581 B2 | 7/2006 | Yamashita et al. | |
| 7,163,545 B2 | 1/2007 | Yaszemski et al. | |
| 7,465,705 B2 | 12/2008 | Lee et al. | |
| 7,507,570 B2 | 3/2009 | Prabhakar et al. | |
| 7,560,106 B2 | 7/2009 | Sasisekharan et al. | |
| 2003/0040112 A1 | 2/2003 | Muir et al. | |
| 2003/0072749 A1 | 4/2003 | Muir et al. | |
| 2003/0077258 A1 | 4/2003 | Muir | |
| 2004/0033221 A1 | 2/2004 | Masuda et al. | |
| 2004/0265297 A1 | 12/2004 | Gruskin et al. | |
| 2005/0118157 A1 | 6/2005 | McMahon et al. | |
| 2005/0233419 A1 | 10/2005 | Pojasek et al. | |
| 2006/0078959 A1 | 4/2006 | Prabhakar et al. | |
| 2006/0153827 A1 | 7/2006 | Gruskin et al. | |
| 2006/0233782 A1 | 10/2006 | Gruskin et al. | |
| 2007/0104703 A1 | 5/2007 | Caggiano et al. | |
| 2007/0274979 A1 | 11/2007 | Gruskin et al. | |
| 2011/0250631 A1 | 10/2011 | Gruskin et al. | |
| 2012/0207732 A1 | 8/2012 | Gruskin et al. | |
| 2012/0308547 A1 | 12/2012 | Caggiano et al. | |
| 2013/0210082 A1 | 8/2013 | Caggiano et al. | |

FOREIGN PATENT DOCUMENTS

| | | |
|---|---|---|
| AU | 2003/208466 B2 | 9/2003 |
| AU | 2003/265561 A1 | 3/2004 |
| AU | 2004/241088 A1 | 12/2004 |
| AU | 2006/294755 B2 | 4/2012 |
| CA | 2623635 C | 4/2013 |
| EP | 0704532 A2 | 4/1996 |
| EP | 1631234 A2 | 3/2006 |
| EP | 1646353 A2 | 4/2006 |
| EP | 2353606 A2 | 8/2011 |
| EP | 2354155 A2 | 8/2011 |
| JP | H06 (1994)-153947 | 6/1994 |

(Continued)

OTHER PUBLICATIONS

Chau et al. "Chondroitinase ABC Enhances Axonal Regrowth Through Schwann Cell-seeded Guidance Channels After Spinal Cord Injury" Nov. 20, 2003 *FASEB J.* 18(1):1-24 (XP003008297).

(Continued)

*Primary Examiner* — Taeyoon Kim

(74) *Attorney, Agent, or Firm* — Pepper Hamilton LLP

(57) ABSTRACT

A method for modifying access of cells to extravascular spaces and regions comprising administering to a patient an enzyme that cleaves chondroitin sulfate proteoglycans is provided. It has been found that administration of an enzyme that cleaves chondroitin sulfate proteoglycans to a patient disrupts extravasation of cells from the blood stream into tissue. The present invention provides methods of reducing penetration of cells associated with inflammation into tissue of a patient. Several methods are also provided for the regulation and suppression of inflammation comprising administering enzymes that digest chondroitin sulfates. Also provided are methods of treating and preventing inflammation associated with infection, injury and disease.

5 Claims, 2 Drawing Sheets

(56) References Cited

FOREIGN PATENT DOCUMENTS

| JP | H09 (1997) 505807 | 6/1997 |
|---|---|---|
| JP | H10 (1998) 506263 | 6/1998 |
| JP | H10-174598 | 6/1998 |
| JP | H11 (1999)-500308 | 1/1999 |
| JP | H11 (1999)-236336 | 8/1999 |
| JP | 2002-505873 | 2/2002 |
| JP | 2002-526028 | 8/2002 |
| JP | 2003-500016 | 1/2003 |
| JP | 2004-89191 | 3/2004 |
| JP | 2004-113166 | 4/2004 |
| WO | WO 91/06303 A | 5/1991 |
| WO | WO 94/25567 A1 | 11/1994 |
| WO | WO 95/13091 A1 | 5/1995 |
| WO | WO 99/40787 A1 | 8/1999 |
| WO | WO 99/46368 A2 | 9/1999 |
| WO | WO 00/52149 A1 | 9/2000 |
| WO | WO 00/62067 A1 | 10/2000 |
| WO | WO 00/64482 A1 | 11/2000 |
| WO | WO 00/075319 A1 | 12/2000 |
| WO | WO 01/39795 A2 | 6/2001 |
| WO | WO 02/08285 A2 | 1/2002 |
| WO | WO 02/055684 A | 7/2002 |
| WO | WO 02/065136 A2 | 8/2002 |
| WO | WO 02/083179 A2 | 10/2002 |
| WO | WO 03/000901 A2 | 1/2003 |
| WO | WO 03/015612 A2 | 2/2003 |
| WO | WO 03/22882 A2 | 3/2003 |
| WO | WO 03/31578 A2 | 4/2003 |
| WO | WO 03/074080 A1 | 9/2003 |
| WO | WO 03/100031 A2 | 12/2003 |
| WO | WO 03/102160 A2 | 12/2003 |
| WO | WO 2004/017044 A2 | 2/2004 |
| WO | WO 2004/103299 A2 | 12/2004 |
| WO | WO 2004/108069 A2 | 12/2004 |
| WO | WO 2004/110359 A2 | 12/2004 |
| WO | WO 2004/110360 A2 | 12/2004 |
| WO | WO 2005/112986 A2 | 12/2004 |
| WO | WO 2005/087920 A2 | 9/2005 |
| WO | WO 2007/038548 A2 | 4/2007 |
| WO | WO 2008/045970 A2 | 4/2008 |

OTHER PUBLICATIONS

Dimayuga et al. "The Neuregulin GGF2 Attenuates Free Radical Release from Activated Microglial Cells" Mar. 2003, *J. Neuroim.* 136(1-2):67-74 (XP002651543).
European Search Report for EP11152626 dated Jul. 21, 2011.
European Search Report for EP10184697 dated Jul. 12, 2011.
Grandpre et al. "Nogo-66 Receptor Antagonist Peptide Promotes Axonal Regeneration" May 30, 2002, *Nature* 417(6888):547-551 (XP002651544).
Hunt et al. "The Nogo Receptor, Its Ligands and Axonal Regeneration in the Spinal Cord; a Review" Feb. 2002, *J. Neurocytology* 31(2):93-120 (XP002651545).
Roy et al. "Treatment with Recombinant Chondroitinases AC and B Permits Neuronal Outgrowth Over Inhibitory Chondroitin Sulfate Proteoglycans (CSPGs)" Nov. 7, 2002, *Society for Neuroscience Abstract Archives* 2000-2005 (Abstract) (XP009150388).
Daichi "Text Book of Physiology" 2000, 3rd Ed. 81.
Accession P59807, Aug. 15, 2003 *UniProtKB/Swiss-Prot.*
Aldrich "Enzymer Explorer" 2009, URL:http://www.sigmaaldrich.com/life-science/metabolomics/enzyme-explorer/learning-center/carbohydrate-analysis/carbohydrate-analysis-iii.
Anderson et al. "Tumor Cell Retention of Antibody Fab Fragments is Enhanced by an Attached HIV TAT Protein-Derived Peptide" 1993, *Biochem. & Biophys. Res. Commun.* 194(2):876-884.
Appel et al. "Several Extracellular Domains of the Neural Cell Adhesion Molecule L1 are Involved in Neurite Outgrowth and Cell Body Adhesion" 1993, *J. Neurosc.* 13(11): 4764-4775.
Avrameas et al. "Polyreactive anti-DNA monoclonal antibodies and a derived peptide as vectors for the intracytoplasmic and intranuclear translocation of macromolecules" 1998, *Proc. Natl. Acad. Sci. USA* 95:5601-5606.
Banker et al. "Modern Pharmaceutics" 1979, *Marcel Dekker, Inc.* (TOC).
Banker et al. "Modern Pharmaceutics" 2002, 4th Ed., *Informa Healthcare, New York* (TOC).
Bao et al. "A Functional Dermatan Sulfate Epitope Containing Iduronate (2-O-sulfate) α1-3GaINAC (6-O-sulfate) Disaccharide in the Mouse Brain" 2005, *J. of Bio. Chem.* 280(24):23184-23193.
Basso et al. "A Sensitive and Reliable Locomotor Rating Scale for Open Field Testing in Rats" 1995, *J. of Neurotrama* 12(1):1-21.
Ben-Bassat et al. "Processing of the Initiation Methionine from Proteins: Properties of the *Escherichia coli* Methionine Aminopeptidase and Its Gene Structure" 1987, *J. Bacteriol.* 169(2):751-757.
Bixby et al. "Neurite outgrowth on muscle cell surfaces involves extracellular matrix receptors as well as Ca2+-dependent and -independent cell adhesion molecules" 1987, *Proc. Natl. Acad. Sci. USA* 84:2555-2559.
Blight et al. "Animal models of spinal cord injury" 2002, *Top Spinal Cord Inj. Rehabi.* 6(2):1-13.
Bowie et al. "Deciphering the Message in Protein Sequences: Tolerance to Amino Acid Substitutions" 1990, *Science* 247:1306-1319.
Bradbury et al. "Chondroitinase ABC Promotes Functional Recovery After Spinal Cord Injury" 2002, *Nature* 416:636-640 (XP002245003).
Bradbury et al. "Chondroitinase ABC Promotes Regeneration and Functional Recovery Following Spinal Cord Injury" 2001, *Soc. for Neuroscience Abstracts* 27(2):1835 (XP002244997).
Bradbury et al. "NT-3 Promotes Growth of Lesioned Adult Rat Sens Ory Axons Ascending in the Dorsal Columns of the Spinal Cord" 1999, *Eur. J. Neurosc.* 11(11):3873-3783.
Bray et al. "Neuronal and Nonneuronal Influences on Retinal Ganglion Cell Survival, Axonal Regrowth, and Connectivity after Axotomy" 1991, *Ann. NY Acad. Sci.*, 214-228.
Broach et al. "Experimental Manipulation of Gene Expression" M. Inouye ed., *Academic Press, New York*, pp. 83-117, 1983.
Burgess et al. "Possible Dissassociation of the Heparin-binding and Mitogenic Activities of Heparin-binding (Acidic Fibroblast) Growth Factor-1 From Its Receptor-binding Activities by Site-directed Mutagenesis of a Single Lysine Residue" 1990, *J. of Cell. Bio.* 111:2129-2138.
Cadelli et al. "Oligodendrocyte- and Myelin-Associated Inhibitors of Neurite Outgrowth: Their Involvement in the Lack of CNS Regeneration" 1992, *Exp. Neur.* 115:189-192.
Caggiano et al. "Chondroitinase ABCI Improves Locomotion and Bladder Function following Contusion Injury of the Rat Spinal Cord" 2005, *J. Neurotrauma* 22(2):226-239.
Cajal "Degeneration & Regeneration of the Nervous System" May 1959 ed., *Hafner Publ. Co., New York* (TOC).
Chang et al. "Extension of Neurites on Axons is Impaired by Antibodies against Specific Neural Cell Surface Glycoproteins" 1987, *J. Cell. Biol.* 104:355-362.
Chen et al. "Peripheral nerve regeneration using silicone rubber chambers filled with collagen, laminin and fibronectin" 2000, *Biomat.* 21:1541-1547.
Crespo et al. "How Does Chondroitinase Promote Functional Recovery in the Damaged CNS?" 2007, *Ex. Neurology* 206:159-171.
Curinga et al. "Mammalian-produced Chondroitinase AC Mitigates Axon Inhibition by Chondroitin Sulfate Proteoglycans" 2007, *J. of Neurochemistry* 102:275-288.
Degrendele et al. "Requirement for CD44 in Activated T Cell Extravassation into an Inflammatory Site" 1997, *Science* 278:672-675.
Denuziere et al. "Chitosan-Chondroitin sulfate and chitosan-hyaluronate polyelectrolyte complexes: biological properties" 1998, *Biomaterials* 19:1275-1285.
Derossi et al. "Cell Internalization of the Third Helix of the Antennapedia Homeodomain is Receptorindependent" 1996, *J. Biol. Chem.* 271:18188-18193.
Doppenberg et al. "Clinical Trials in Traumatic Brain Injury" 1998, *Ann. NY Acad. Sci.* 305-319.
Edelman "Cell Adhesion Molecules" 1983, *Science* 219:450-457.
Edelman et al. "Morphoregulatory Molecules" 1990, *Wiley, New York* (TOC).

(56) References Cited

OTHER PUBLICATIONS

Efthymiadis et al. "The HIV-1 Tat Nuclear Localization Sequence Confers Novel Nuclear Import Properties" Jan. 16, 1998, *J. Biol. Chem.* 273(3):1623-1628.
Ellioit et al. "Intercellular Trafficking and Protein Delivery by a Herpesvirus Structural Protein" 1997, *Cell* 88:223-233.
Fahraeus et al. "Inhibition of pRb phosphorylation and cell-cycle progression by a 20-residue peptide derived from p16CDKN2IINK4A" 1996, *Curr. Biol.* 6(1):84-91.
Favre et al. "Hyaluronidase enhances recombinant adeno-associated virus (rAAV)-mediated gene transfer in the rat skeletal muscle" 2000, *Gene Ther.* 7(16):1417-1420.
Fawcett et al. "The glial scar and central nervous system repair" 1999, *Brain Res. Bull.* 49(6):377-391.
Fawell et al. "Tat-mediated delivery of heterologous proteins into cells" 1994, *Proc. Natl. Acad. Sci. USA* 91:664-668.
Fethiere et al. "Crystal Structure of Chondroitin AC Lyase, a Representative of a family of Glycosaminoglycan Degrading Enzymes" 1999, *J. Mol. Biol.* 288:635-647.
Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.
Frankel et al. "Tat Protein from Human Immunodeficiency Virus Forms a Metal-Linked Dimer" 1988, *Science* 240:70-73.
Frankish et al. "Spinal-cord Repair Moves a Step Closer" 2002, *The Lancet* 359(9314):1317 (XP004792003).
Gennaro "Remington's Pharmaceutical Sciences" 1985, $17^{th}$ Ed., *Mack Publishing Company (PA)* (TOC).
Goodman et al. "The Pharmacological Basis of Therapeutics" 1980, 6th ed., *MacMillan Pub., New York* (TOC).
Goodman et al. "The Pharmacological Basis of Therapeutics" 2001, 10th ed., *McGraw Hill, New York* (TOC).
Hamai et al. "Two Distinct Chondroitin Sulfate ABC Lyases" 1997, *J. Biol. Chem.* 272(14):9123-9130.
Hirschberg et al. "Inflammation after axonal injury has conflicting consequences for recovery of function: rescue of spared axons is impaired but regeneration is supported" 1994, *J. Neuroimmunol.* 50(1):9-16 (Abstract).
Hiyama et al. "Crystallization and Some Properties of Chondroitinase from *Arthrobacter Aurescens*" 1975, *J. Biol. Chem.* 250:1824-1828.
Hlavin et al. "Molecular Structure and Functional Testing of Human L1CAM: An Interspecies Comparison" 1991, *Genomics* 11:416-423.
Hoffman et al. "Chondroitin Sulfates" 1958, *Federation Proc.* 17:1078-1082.
Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.
Hou et al. "Endotoxin Removal by Anion-Exchange Polymeric Matrix" 1990, *Biotech. Appl. Biochem.* 12:315-324.
Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.
Huang et al. "Crystal Structure of Chondroitinase B from Flavobacterium heparinum and its Complex with a Disaccharide Product at 107 A Resolution" 1999, *J. Mol. Biol.* 294:1257-1269.
Huang et al. "Crystal Structure of *Proteus vulgaris* Chondroitin Sulfate ABC Lyase I at 1.9 A Resolution" 2003, *J. Mol. Biol.* 328:623-634.
Iida et al. "Cell Surface Chondroitin Sulfate Proteoglycans in Tumor Cell Adhesion, Motility and Invastion" 1996, *Seminars in Cancer Biology* 7:155-162.
Iwai et al. "Axon Patterning Requires DN-cadherin, a Novel Neuronal Adhesion Receptor, in the *Drosphila* Embryonic CNS" 1997, *Neuron* 19:77-89.
Jones "Taking a new TAK on Tat transactivation" 1997, *Genes & Dev.* 11:2593-2599.

Jung et al. "Transit time of leutocytes rolling through venules controls cytokine-induced inflammatory cell recruitment in vivo" 1998, *J. Clin. Invest.* 102(8):1526-1533.
Kadmon et al. "Functional Cooperation between the Neural Adhesion Molecules L1 and N-CAM is Carbohydrate Dependent" 1990, *J. Cell Biol.* 110:209-218.
Kadmon et al. "The Neural Cell Adhesion Molecule N-CAM Enhances L1-dependent Cell-Cell Interactions" 1990, *J. Cell Biol.* 110:193-208.
Khan et al. "Animal Models of Spinal Cord Contusion Injuries" 1999, *Laboratory Animal Science* 49(2): 161-172.
Kim et al. "Insertion and Deletion Mutants of FokI Restriction Endonuclease" 1994, *J. Biol. Chem.* 269(50):31978-31982.
Korn, 1957 "The Degradation of Heparin by Bacterial Enzymes" *J. Biol. Chem.* 226:841-844.
Krekoski et al. "Axonal Regeneration into Acellular Nerve Grafts is Enhanced by Degradation of Chondroitin Sulfate Proteoglycan" 2001, *J. Neurosci.* 15:21(16):6206-6213.
Kubota et al. "Functional Similarity of HIV-1 Rev and HTLV-1 Rex Proteins: Identification of a New Nucleolar-Targeting Signal in Rev Protein" Aug. 15, 1989, *Biochem. Biophys. Res. Commun.* 162(3):963-970.
Kwon et al. "Animal Models Used in Spinal Cord Regeneration Research" 2002, *Spine* 27(14):1504-1510.
Lagenaur et al. "An L1-like molecule, the 8D9 antigen, is a potent substrate for neurite extension" 1987, *Proc. Natl. Acad. Sci. USA* 84:7753-7757.
Lemons et al. "Chondroitin Sulfate Preteoglycan Immunoreactivity Increases Following Spinal Cord Injury and Transplantation" 1999, *Exper. Neurology* 160:51-65.
Lesley et al. "Variant Cell Lines Selected for Alterations in the Function of the Hyaluronan Receptor CD44 Show Differences in Glycosylation" 1995, *J. Exp. Med.* 182:431-437.
Li et al. "Delayed systemic Nogo-66 Receptor Antagonist Promotes Recovery from Spinal Cord Injury" 2003, *J. Neuroscience* 23(10):4219-4227.
Lindner et al. "L1 mono- and polyclonal antibodies modify cell migration in early postnatal mouse cerebellum" 1983, *Nature* 305:427-430.
Lodish et al. "Integrating cells into tissue" 2000, *Mol. Cell Biology*, 5th Ed., Chapter 6.
Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.
Maniatis et al. "Molecular Cloning: A Laboratory Manual" 1982, *Cold Spring Harbor Lab.* (TOC).
Mann et al. "Endocytosis and Targeting of Exogenous HIV-1 Tat Protein" Jul. 1991, *EMBO J.* 10(7):1733-1739.
Martinez et al. "Purification and Properties of the Enzyme Chondroitinase" 1959, *J. Biol. Chem.* 234(9):2236-2239.
Martini et al. "Restricted Localization of L1 and N-CAM Sites of Contact Between Schwann Cells and Neurites in Culture" 1994, *GLIA* 10:70-74.
Matinysn "Restoration of functions due to Enzyme Therepy After Complete Transaction of the Spinal Cord" 1965, ZH EK SP KLIN MED 5(3):3-13.
Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.
Matteuci et al. "Synthesis of Deoxyoligonucleotides on a Polymer Support" 1981, *J. Am. Chem. Soc.* 103:3185-3191.
McGee et al. "The Nogo-66 Receptor:Focusing Myelin Inhibition of Axon Regeneration" 2003, *Trends in Neuroscience* 26(4):193-198.
Michelacci et al. "A Comparative Study Between a Chondroitinase B and a Chondroitinase AC from Flavobacterium heparinum" 1975, *Biochem. J.* 151:121-129.
Michelacci et al. "Chondroitinase C from Flavobacterium haparinum" 1976, *J. Biol. Chem.* 251(4):1154-1158.
Michelacci et al. "Isolation and characterization of an induced Chondroitinase ABC" 1987, *Biochem. Biophys. Acta* 923:291-301.

(56) References Cited

OTHER PUBLICATIONS

Michelacci et al. "Isolation and Partial Characterization of an Induced Chondroitinase β from Flavobacterium Heparium" 1974, *Biochem. & Biophys. Res. Comm.* 56(4):973-980.

Miller et al. "N-terminal methionine-specific peptidase in *Salmonella* typhimurium" 1987, *PNAS* 84:2718-2722.

Miura et al. "Analysis of Glycosaminoglycan-Degrading Enzymes by Substrate Gel Electrophoresis (Zymography)" 1995, *Anal. Biochem.* 225:333-340.

Modena et al. "Hylauronidase-injectable microparticles intended for the treatment of extravasation" 1998, *J. Microencapsulation* 15(1):85-92.

Moon et al. "Regeneration of CNS axons back to their target following treatment of adult rat brain with chondroitinase ABC" 2001, *Nature Neurosc.* 4(5): 465-466.

Moos et al. "Neural adhesion molecule L1 as a member of the immunoglobulin superfamily with binding domains similar to fibronectin" 1988, *Nature* 334:701-703.

Nagahara et al. "Transduction of fUll-length TAT fusion proteins into mammalian cells: TAT_p27Klp1 induces cell migration" 1998, *Nat. Med.* 4(12):1449-1452.

Netti et al. "Role of Extracellular Matrix Assembly in Interstitial Transport in Solid Tumors" 2000, *Cancer Res.* 60(9):2497-2503.

Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.

Oermann et al. "The Use of Anti-inflammatory Medications in Cystic Fibrosis" 1999, *Chest* 115:1053-1058.

Olmarker et al. "Chondroitinase ABC (Pharmaceutical Grade) for Chemonucleolysis" 1996, *Spine* 21(17):1952-1956.

Pawson et al. "Assembly of Cell Regulatory systems Through Protein Interaction Domains" 2003, *Science* 300:445-452.

Pillwein et al. "Hyaluronidase Additional to Standard Chemotherapy Improves Outcome for Children with Malignant Tumors" 1998, *Cancer Letters* 131:101-108.

Pojasek et al. "Biochemical Characterization of the Chondroitinase B Active Site" Aug. 23, 2002, *J. Biol. Chem.* 277(34):31179-31186.

Pojasek et al. "Recombinant Expression, Purification, and Kinetic Characterization of Chondroitinase AC and Chondroitinase B from Flavobacterium heparinum" 2001, *Biochem, Biophys. Res. Commun.* 286:343-351.

Prabhakar et al. "Biochemical Characterization of the Chondroitinase ABC I Active Site" Aug. 23, 2005, *Biochem. J.*,pp. 395-405.

Priestley et al. "Stimulating regeneration in the damaged spinal cord" 2002, *J. Phyl.* 96:123-133.

Rathjen et al. "Immunocytological and biochemical characterization of a new neuronal cell surface component (L1 antigen) which is involved in cell adhesion" 1984, *EMBO J.* 3(1):1-10.

Ratjen et al. "Cystic Fibrosis" 2003, *The Lancet* 361(9358):681-689 (Presentation).

Reich et al. "Small interfering RNA (siRNA) targeting VEGF effectively inhibits ocular neovascularization in a mouse model" 2003, *Molecular Vision* 9:210-216 (Abstract).

Reid et al. "Variants of Human L1 Cell Adhesion Molecule Arise through Alternate Splicing of RNA" 1992, *J. Mol. Neurosc.* 3:127-135.

Roy et al. "Generation of Substantially Smaller Deletion Mutants of Chondroitinase AC and B Those are Biologically Active" Nov. 8-12, 2003, *Society for Neuroscience Abstract Viewer and Itinerary Planner, 33rd Annual Meeting of the Society of Neuroscience, New Orleans, LA, Database Biosis*, (Abstract).

Saito et al. "Enzymatic Methods for the Determination of Small Quantities of Isomeric Chondroitin Sulfates" 1968, *J. Biol. Chem.* 243(7):1536-1542.

Sambrook et al. "Molecular Cloning" 1989, 2nd ed., *Cold Spring Harbor Laboratory Press* (TOC).

Sambrook et al. "Molecular Cloning" 1989, 2nd ed., *Cold Spring Harbor Laboratory Press, Ch. 16 and 17.*

Sato et al. "Cloning and expression in *Escherichia coli* of the gene encoding the *Proteus vulgaris* chondroitin ABC-lyase" 1994, *Appl. Microbiol. Biotechnol.* 41:39-46.

Sato, et al. "Subunit Structure of Chondroitinase ABC from *Proteus vulgaris*" 1986 *Agric. Biol. Chem.* 50(4):1057-1059.

Schachner "Functional implications of glial cell recognition molecules" 1990, *Neurosc.* 2:497-507.

Schwab "Nerve fibre regeneration after traumatic lesions of the CNS; progress and problems" 1991, *Phil. Trans. R. Soc. Lond.* 331:303-306.

Schwarze et al. "In Vivo Protein Transduction: Delivery of a Biologically Active Protein into the Mouse" 1999, *Science* 285:1569-1572.

Seikagaku Biobus. Corp. "Chondroitinase AC II pamphlet" 2009, URL:http/www.seikagakubb.co.jp/bio/cgi-bin/search/tenpu_pdf/100335.pdf.

Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Biol.* 107:341-351.

Silver et al. "Postnatally induced formation of the corpus callosum in acallosal mice on glia-coated cellulose bridges" 1983, *Science* 220:1067-1069.

Smiseth et al. "Effect of Hyaluronidase on Substrate Exchange and Blood Flow in the Ischaemic Myocardium of the Dog" 1982, *Clinical Physiology* 2(1):39-50.

Smith-Thomas et al. "Increased Axon Regeneration in Astrocytes Grown in the Presence of Proteoglycan Synthesis Inhibitors" 1995, *J. of Cell Science* 108(3):1307-1315.

Southern "Detection of Specific Sequences Among DNA Fragments Separated by Gel Electrophoresis" 1975, *J. Mol. Biol.* 98:503-517.

Stedman's Medical Dictionary 2000, *Lippincott Williams & Wilkins, 27th Ed.*

Sterne et al. "Neurotrophin-3 Delivered Locally via Fibronectin Mats Enhances Peripheral Nerve Regeneration" 1997, *Eur. J. Neurosc.* 9:1388-1396.

Tona et al. "Effect of Hyaluronidase on Brain Extracellular Matrix in Vivo and Optic Nerve Regeneration" 1993, *J. Neurosc. Res.* 36:191-199.

Trigg et al. "Peripheral Nerve Regeneration: Comparison of Laminin and Acidic Fibroblast Growth Factor" 1998, *Am. J. Otolaryngology* 19(1):29-32.

Tsuda et al. "Substrate Specificity Studies of Flavobacterium Chondroitinase C and Heparitinases Towards the Glycosaminoglycan-protein Linkage region" 1999, *European J. of Biochem.* 262:127-133.

Vives et al. "A Truncated HIV-1 Tat Protein Basic Domain Rapidly Translocates through the Plasma Membrane and Accumulates in the Cell Nucleus" 1997, *J. Biol. Chem.* 272(25):16010-16017.

Vives et al. "Effects of the Tat Basic Domain on Human Immunideficiency Virus Type 1 Transactivation, Using Chemically Synthesized Tat Protein and Tat Peptides" May 1994, *J. Virol.* 68(5):3343-3353.

Williams et al. "Calcium Influx into Neurons Can Solely Account for Cell Contact-dependent Neurite Outgrowth Stimulated by Transfected L1" 1992, *J. Cell Biol.* 119(4):883-892.

Wood et al. "Inhibition of Schwann Cell Myelination in vitro by Antibody to the L1 Adhesion Molecule" 1990, *J. Neurosc.* 10(11):3635-3645.

Yamagata et al. "Purification and Properties of Bacterial Chondroitinases and Chondrosulfatases" 1968, *J. Biol. Chem.* 243(7):1523-1535.

Yamagata et al. "Repression of a Malignant Cell-Substratum Adhesion Phenotype by Inhibiting the Production of the Anti-Adhesive Proteoglycan, PG-M/Versican" 1994, *J. of Cell Science* 1007:2581-2590.

Yang et al. "Developmental Regulation of a Matrix Metalloproteinase during Regeneration of Axolotl Appendages" 1994, *Dev. Biol.* 166:696-703.

Yang et al. "Expression of Mmp-9 and Related Matrix Metalloproteinase Genes During Axolotl Limb Regeneration" 1999, *Dev. Dyn.* 216:2-9.

Yasuda et al. "Effect of Hyluronidase on Experimental Cerebral Infarct Size and Mortality" 1982, *Lab. Invest.* 46:400-404.

Yick et al. "Chondroitinase ABC promotes axonal regeneration of Clarke's neurons after spinal cord injury" 2000, *Regeneration and Transpl.* 11(5):1063-1067.

(56) References Cited

OTHER PUBLICATIONS

Yick et al. "Chondroitinase ABC Promotes Axonal Regrowth of Clarke's Neurons Into Peripheral Nerve Graft After Hemisection of the Spinal Cord" 1999, *Soc. for Neuroscience Abstracts* 25:747.

Zuo et al. "Degradation of Chondroitin Sulfate Proteoglycan Enhances the Neurite-Promoting Potential of Spinal Cord Tissue" 1998, *Exp. Neurol.* 154(2):654-662 (XP003008298).

Zuo et al. "Regeneration of Axons After Nerve Transection Repair is Enhanced by Degradation of Chondroitin Sulfate Proteoglycan" 2002, *Exp. Neurology* 176:221-228.

METHODS OF REDUCING EXTRAVASATION OF INFLAMMATORY CELLS

CROSS-REFERENCE TO RELATED APPLICATIONS

This application is a divisional application of pending U.S. application Ser. No. 10/847,636, filed May 17, 2004, which claims priority to U.S. Provisional Application No. 60/471,189, filed May 16, 2003, each of which are herein incorporated by reference in their entirety.

BACKGROUND

1. Field of the Invention

The present disclosure relates to methods of reducing penetration of inflammatory cells into tissue, in particular to methods of reducing extravasation of macrophage cells from blood vessels, methods of preventing, regulating and suppressing inflammatory response, and methods of treating inflammatory states.

2. Description of Related Art

The inflammatory response evolved to protect organisms against injury and infection. Following an injury or infection, a complex cascade of events leads to the delivery of blood-borne leukocytes to sites of injury to kill potential pathogens and promote tissue repair. However, the powerful inflammatory response has the capacity to cause damage to normal tissue, and dysregulation of the innate or acquired immune response is involved in different pathologies. It has long been known that Multiple Sclerosis is an inflammatory disease of the brain, but it is only in recent years that it has been suggested that inflammation may significantly contribute to diseases such as stroke, traumatic brain injury, HIV-related dementia, Alzheimer's disease and prion disease. The recognition of an inflammatory component in the pathology of these and other diseases has come from the development of new techniques and reagents for the study of inflammation biology.

The inflammatory response is a part of innate immunity. Inflammation occurs when tissues are injured by viruses, bacteria, trauma, chemicals, heat, cold, or any other harmful stimuli. Chemicals, such as bradykinin, histamine, and serotonin, are released by specialized cells and attract tissue macrophages and white blood cells to localize in an area to engulf (phagocytize) and destroy foreign substances. A byproduct of this activity is the formation of pus—a combination of white blood cells, bacteria, and foreign debris. The chemical mediators released during the inflammatory response give rise to the typical findings associated with inflammation.

Inflammation constitutes the body's response to injury and is characterized by a series of events that includes the inflammatory reaction per se, a sensory response perceived as pain, and a repair process. The inflammatory reaction is characterized by successive phases: (1) a silent phase, where cells, including resident cells in the damaged tissue, release the first inflammatory mediators, (2) a vascular phase where vasodilation and increased vascular permeability occur, and (3) a cellular phase, which is characterized by the infiltration of leukocytes to the site of injury. The repair process includes tissue cell division, neovascularization and reinnervation of repaired tissues. In many diseases such as arthritis, inflammatory bowel disease, and asthma, the inflammatory process is not appropriately regulated. As a result, significant tissue dysfunction (leading to the generation of the symptoms that typify these diseases), and tissue re-structuring occur (e.g., fibrosis) that can further impair tissue function.

The very first event of the inflammatory reaction, the "silent phase" is based upon the reaction of cells and resident cells of the damaged tissue. These resident cells release mediators, such as nitric oxide (NO), histamine, kinins, cytokines, or prostaglandins. The release of these vasomotor mediators from resident cells leads to the second phase of the inflammatory reaction: the vascular phase. Vascular tone and permeability are regulated by an endothelial-dependent mechanism involving the release of nitric oxide. Certain agonist signal to sensory afferents, including the release of neuropeptides which are known to act on vascular beds to induce vasodilation and increased permeability. Increased vasodilatation and permeability provoke plasma leakage from the blood to the inflamed tissues, and facilitate the passage of leukocytes from the blood flow to the tissues.

The third phase of the inflammatory process is the cellular phase, which is characterized by the arrival of leukocytes circulating in the blood. In order to be recruited to the site of inflammation, circulating leukocytes roll onto the venular endothelial surfaces, adhere to the endothelium, and then transmigrate across the endothelial barrier. The process by which cells leave the blood stream and penetrate tissue parenchyma is known as extravasation. The events of rolling, adhesion, and transmigration (extravasation) are regulated by several cell adhesion molecules, known as CAMs and receptor molecules expressed by the endothelium and the leukocytes.

The inflammatory response to tissue damage may be of great value. By isolating the damaged area, mobilizing effector cells and molecules to the site, and—in the late stages—promoting healing, inflammation may protect the body. However, inflammation is more often associated with pain, injection and diseased states. Often the inflammatory response is out of proportion to stimulus which activated the response. The inflammatory process inevitably causes tissue damage and is accompanied by simultaneous attempts at healing and repair. Tissue destruction is caused by both the caustic agents and by the inflammatory process itself. The result can be more damage to the body than the agent itself would have produced. For example, all the many types of allergies and many of the autoimmune diseases are examples of inflammation in response to what should have been a harmless, or at least a noninfectious, agent. Some examples of chronic inflammatory diseases include Asthma, Rheumatoid Arthritis (RA), Multiple Sclerosis (MS), Systemic Lupus Erythematosus (SLE), psoriasis, and Chronic Obstructive Pulmonary Disease (COPD). In many of these cases, the problem is made worse by the formation of antibodies against self antigens or persistent antigens from smoldering infections. Additionally, any disease with an inflammatory component may be treated by a better understanding of the immune system and the disease-fighting responses to toxins, injury, viruses and bacteria. Recently, it has been shown that inflammation has been link to cardiovascular diseases.

Traditional therapeutics for the treatment of inflammation include anti-inflammatory agents and steroids. Inappropriate inflammation can be treated with steroids like the glucocorticoid cortisol, nonsteroidal anti-inflammatory drugs (NSAIDs) like aspirin and ibuprofen, and a number of proteins produced by recombinant DNA technology.

The NSAIDs achieve their effects by blocking the activity of cyclooxygenase. The body produces several different forms of cyclooxygenase (COX), including COX-1, which is involved in pain, clotting, and protecting the stomach; COX-2, which is involved in the pain produced by inflammation. Most of the NSAIDs inhibit both COX-1 and COX-2. However, some newer drugs, the so-called COX-2 inhibitors, such as rofecoxib (Vioxx®) and celecoxib (Celebrex®) are much more active against COX-2 than COX-1.

Recombinant DNA and monoclonal antibody technology have produced some new therapies that are being enlisted in the battle against damaging inflammation. Examples of these therapeutics include: (1) an IL-1 antagonist that binds and inactivates the IL-1 receptor; (2) etanercept (Embrel®), which a soluble version of the TNF-α receptor, which binds TNF-α preventing it from carrying out its many inflammatory actions; (3) recombinant protein C, which helps the body dissolve the tiny clots that are triggered during inflammation; (4) infliximab (Remicade®), which is a monoclonal antibody that binds to TNF-α, particularly promising against some inflammatory diseases such as rheumatoid arthritis; and (5) the antibody natalizumab (Antegren®; Biogen Inc., Cambridge Mass.), which functions by blocking the adhesion of immune cells to blood vessels and can inhibit movement of immune cells from the blood into the brain. Several of these therapies carry a severe risk of allowing infections to develop. In fact, the more powerful the anti-inflammatory agents (e.g., glucocorticoids), the greater the risk of infection.

Reducing inflammation and regulating the inflammatory response also is beneficial in the prevention of various cancers and other cell conditions. Chronic inflammation is a recognized cause of cancer. For example, liver cancer is often the sequel to years of inflammation caused by infection hepatitis B or C infection. Lung cancer often is the end stage of years of chronic inflammation caused by inhaled irritants, such as tobacco smoke. Cervical cancer can follow chronic infection and inflammation caused by papilloma viruses and chlamydia. Similarly, bladder, colon, pancreas, stomach, and other cancers may be the final stage of years of inflammation.

The strong link between chronic inflammation and cancer should not be surprising considering that the reactive oxygen species (ROS) liberated during inflammation are powerful DNA-damaging agents. Additionally, increased mitosis in response to inflammation puts more cells at risk of mutations as they replicate their DNA during S phase. Furthermore, apoptosis, the programmed death of damaged cells, is suppressed in inflamed tissue. So precancerous cells with genetic mutations, which should have committed suicide, continue and ultimately develop into cancerous cells. Therefore, the regulation of the inflammatory response including reducing inflammation in tissues is beneficial to the prevention of various cancers.

The penetration of inflammatory cells into and through the parenchyma of tissues is intimately involved in the pathophysiology of numerous disease, injury and inflammatory states. The ability to prevent penetration of inflammatory cells into tissue has beneficial therapeutic effects. It is known that reduction of tissue penetrating inflammatory cells has been accomplished to a degree with steroid, anti-integrin and other anti-inflammatory compounds. The access of cells through the blood vessel wall and into tissues is, in part, dependent upon the extracellular matrix, receptor molecules, CAMs, the cell membranes of the vascular endothelium and the migrating cell. Interfering with one or more of these signals or receptors disrupts the recruitment of inflammatory cells to the tissue. This disruption thus leads to reduced inflammation in the tissue.

SUMMARY OF THE INVENTION

It has been found that the use of enzymes capable of cleaving chondroitin sulfate proteoglycans are effective in altering the extravasation of cells associated with inflammation, such as macrophages from blood vessels into tissue.

One embodiment of the present invention is a method for modifying access of cells to extravascular spaces and regions comprising administering to a patient an enzyme that cleaves chondroitin sulfate proteoglycans. Another embodiment of the present invention is a method of reducing penetration of cells associated with inflammation into tissue of a patient. In several methods of the invention, an enzyme selected from the group consisting of chondroitinase $ABC_{Type\ I}$, chondroitinase $ABC_{Type\ II}$, chondroitinase AC, chondroitinase B, Hyaluronidase 1, Hyaluronidase 2, Hyaluronidase 3, Hyaluronidase 4, and hyaluronoglucosaminidase, fragments thereof, and combinations thereof are used. In several embodiments of the invention enzymes directed against integrins containing chondroitin sulfate proteoglycan expressed on the cell surface of cells are used.

Another embodiment of the present invention is a method for inhibiting extravasation of cells associated with inflammation from blood vessels comprising administering to a patient an enzyme that cleaves chondroitin sulfate proteoglycans. In several embodiments of the invention an enzyme prevents cells selected from the group selected from the group consisting of white blood cells, leukocytes, neutrophils, eosinophils, basophils, lymphocytes, B-cells, T-cells, monocytes, and macrophages cells from leaving the blood stream.

Another embodiment of the invention is a method of treating inflammation in a patient comprising administering to the patient an enzyme that cleaves chondroitin sulfate proteoglycans. In several embodiments of the present invention, inflammation is associated with disease or injury, such as chronic inflammatory diseases and central nervous system disease.

Another embodiment of the invention is a method of preventing inflammation in a patient comprising administering to the patient an enzyme that cleaves chondroitin sulfate proteoglycans.

Another embodiment of the present invention is a method of treating inflammation of a patient comprising extracting cells associated with inflammation from a patient, subjecting the cells to an enzyme that cleaves chondroitin sulfate proteoglycans ex vivo to modify the cells, and administering the modified blood cells into the patient.

BRIEF DESCRIPTION OF THE DRAWINGS

For a fuller understanding of the nature and advantages of the present invention, reference should be had to the following detailed description taken in connection with the accompanying drawings, in which.

DETAILED DESCRIPTION

Figure 1:
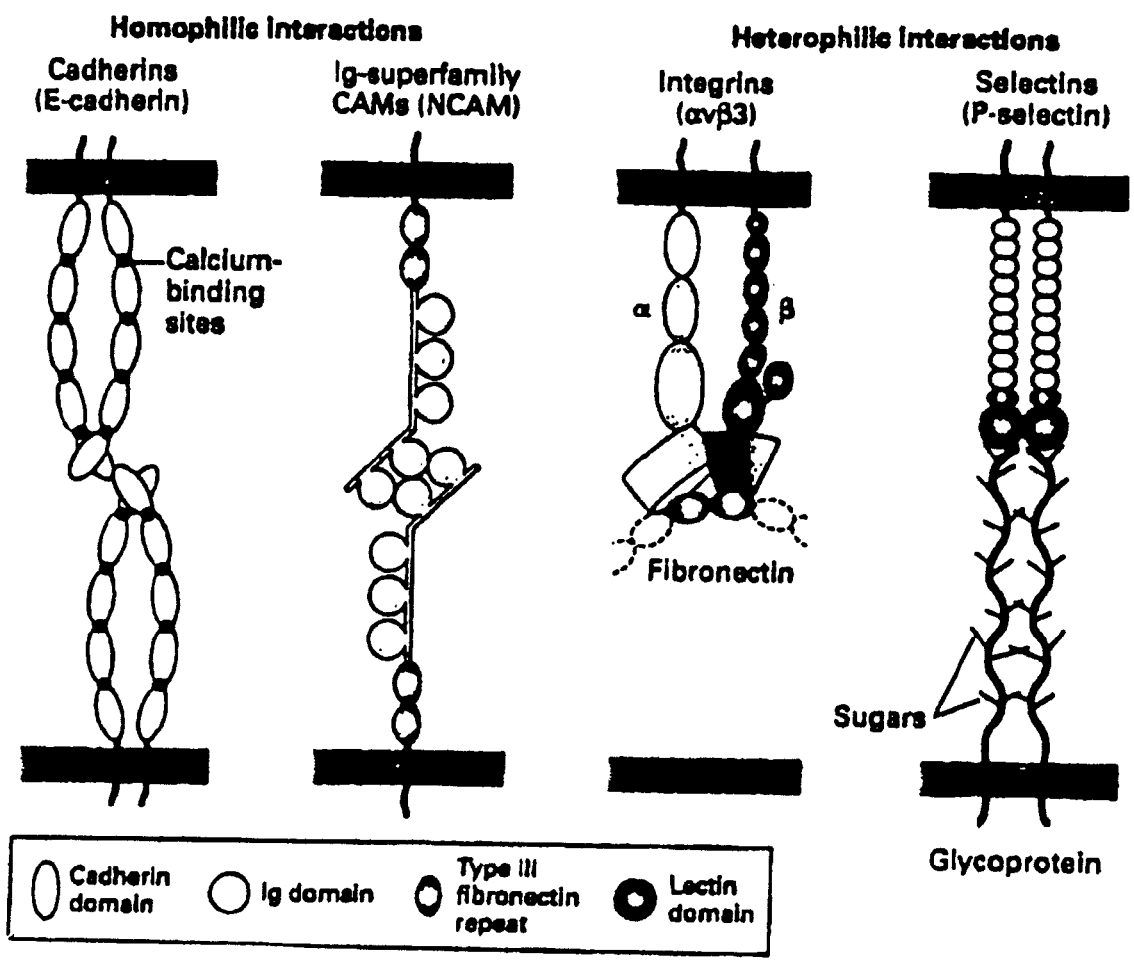
FIG. 1 is schematic drawing of the four major families of cell adhesion molecules.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "enzyme" is a reference to one or more enzymes and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It has been found that the administration of certain enzymes to the blood stream disrupts the mechanism by which cells move from the blood stream to the tissues. When cells, primarily macrophages and other immunological cells or cells associated with inflammation, are signaled to enter a tissue, extravasation ensues. The cells circulating in the blood stream migrate to the blood vessel walls where they encounter specific receptors, known as cell adhesion molecules. Through specific receptor based adhesion to the vessel wall, the cells roll along the wall until they encounter an endothelial cell junction where they can squeeze out of the vessel and enter the extravascular space. Some of these adhesion molecules or receptors contain carbohydrate chains made up of chondroitin sulfates. Digestion of these chains with enzymes interrupts extravasation. Several methods are provided for the regulation, prevention, treatment and suppression of the inflammatory response comprising administering enzymes that digest chondroitin sulfates. Also provided are methods of treating and preventing infection and diseases associated with inflammatory response.

The process of "extravasation" is known as the transmigration of cells, such as leukocytes, from a blood vessel into the extravascular space, and may further include migration into surrounding tissue. As used herein the term "leukocyte" is used to refer to the class of cells associated with inflammation, which may also be defined as any of the various blood cells that have a nucleus and cytoplasm. Also known as white blood cells, leukocytes include neutrophils, eosinophils, basophils, lymphocytes, such as B-cells, T-cells, monocytes and macrophages. Four types of leukocytes are particularly important in immune defense, including neutrophils, which release several antibacterial proteins; monocytes, which are the precursors of macrophages that engulf and destroy foreign particles, and T and B lymphocytes, which are the antigen-recognizing cells of the immune cells.

The term "therapeutic agent" used in connection with the inflammatory response therefore means an agent that functions as a blocker, suppressor, regulator or modulator of the inflammatory response. For example, several therapeutic enzymes described herein function as blockers, suppressors, regulators or modulators of the inflammatory response.

Inflammation is a defense reaction caused by tissue damage or injury, characterized by redness, heat, swelling, and pain. The inflammatory response involves the dilation of capillaries to increase blood flow; microvascular structural changes and escape of plasma proteins from the bloodstream; and leukocyte transmigration through endothelium and accumulation at the site of injury. As explained above, the ability to control the inflammatory response is beneficial in reducing inflammation associated with disease or infection and is also beneficial in treating a number of diseases with an inflammatory component.

Several types of leukocytes participate in the defense against infection caused by foreign invaders (e.g., bacteria and viruses) and tissue damage due to trauma or inflammation. To fight infection and clear away damaged tissue, these cells must move rapidly from the blood stream, where they circulate as unattached, relatively quiescent cells, into the underlying tissue at sites of infection, inflammation or damage.

Extravasation requires the successive formation and breakage of cell-cell contacts between leukocytes in the blood and endothelial cells lining the vessels. This successive formation and breakage is also known as the "leukocyte adhesion cascade", which is described as a sequence of adhesion and activation events that ends with extravasation of the leukocyte, whereby the cell exerts its effects on the inflamed tissue site. Some sources have described the cascade as having at least five steps of adhesion termed capture, rolling, slow rolling, firm adhesion, and transmigration. For example, R. O. Hynes and A. Lander, 1992, *Cell* 68:3030, herein incorporated by reference, describes the sequence in five steps. See also, Jung U, Norman K•E, Scharffetter-Kochanek K, Beaudet A L, Ley K, Transit Time of Leukocytes Rolling through venules Controls Cytokine-induced Inflammatory Cell Recruitment In Vivo. *Journal of Cinical Investigation.* 1998; 102:1526-1533, herein incorporated by reference. Each of these five steps appears to be necessary for effective leukocyte recruitment, therefore blocking any of the five can severely reduce leukocyte accumulation in the tissue. These steps are not phases of inflammation, but represent the sequence of events from the perspective of each leukocyte. At any given moment, the events of capture, rolling, slow rolling, firm adhesion and transmigration occur in parallel, involving different leukocytes in the same microvessels.

Cells in tissue can adhere directly to one another (cell-cell adhesion) through specialized integral membrane proteins called cell-adhesion molecules (CAMs). There are four principal classes of CAMs: cadherins (or mucins), the immunoglobulin (Ig) superfamily, selectins, and integrins. See for example, "Molecular Cell Biology", 5th Edition, Lodish, et al. Chpt 6, "Integrating Cells into Tissue", herein incorporated by reference in its entirety, which describes the general categories of CAMs. FIG. 1 is a schematic drawing of these four major categories of CAMs. CAMs mediate through their extracellular domains adhesive interactions between cells of the same type or between cells of a different type. The homophilic interactions are coordinated by the cadherins and the Ig-superfamily. While the heterophilic interactions occur with integrins and selectins.

The structures of the various CAMs vary according to function. The selectins, shown as dimers in FIG. 1, contain a carbohydrate-binding lectin domain that recognizes specialized sugar structures on glycoproteins (shown here) and glycolipids on adjacent cells.

Selectins mediate leukocyte-vascular cell interactions. For example, P-selectin is localized to the blood-facing surface of endothelial cells. Selectins contain a $Ca^{2+}$-dependent lectin domain, which is located at the distal end of the extracellular region of the molecule and recognizes oligosaccharides in glycoproteins or glycolipids. For example, the primary ligand for P- and E-selectins is an oligosaccharide called the sialyl Lewis-x antigen, a part of longer oligosaccharides present in abundance on leukocyte glycoproteins and glycolipids. P-selectin exposed on the surface of activated endothelial cells mediates the weak adhesion of passing leukocytes. Because of the force of the blood flow and the rapid "on" and "off" rates of P-selectin binding to its ligands, these trapped leukocytes are slowed but not stopped and literally roll along the surface of the endothelium. Among the signals that promote activation of the endothelium are chemokines, a group of small secreted proteins produced by a wide variety of cells, including endothelial cells and leukocytes.

All known selectin ligands are transmembrane glycoproteins which present oligosaccharide structures to the selectins. Transient bond formations between the selectins and their ligands mediate the early steps of the adhesion cascade. All three selectins can recognize glycoproteins and/or glycolipids containing the tetrasaccharide sialyl-Lewis$^x$ (sialyl-CD15). This tetrasaccharide is found on all circulating myeloid cells and is composed of sialic acid, galactose, fucose, and N-acetyl-galactosamine.

PSGL-1 (P-selectin Glycoprotien Ligand) has been characterized as a ligand for P-selectin. PSGL-1 is a glycoprotein expressed on blood cells and contains the sialyl-Lewis$^x$ tetrasaccharide. Another P-selectin ligand is CD24, which appears to be important for tumor cell binding to P-selectin. For L-selectin, four possible ligands have been identified: GlyCAM-1 (Glycosylation-Dependent Cell Adhesion Molecule), CD34, and MAdCAM-1 (Mucosal Addressin Cell Adhesion Molecule), and PSGL-1. Evidence suggests that both sulfate and sialic acid in an $\alpha(2,3)$ linkage are essential to L-selectin ligand activity. Although specific ligands for E-selectin are not yet known, candidate molecules include fucosylated, sialyated oligosaccharides found as components of glycoprotein and glycolipid molecules.

The P-, E-, and L-selectins have long chains of short consensus repeats, such as SRC, also found in complement regulating proteins. These long chains reach out from the cell surface and at the end of the SRC chain there is a EGF domain and finally the C-type lectin domain. The S-type selectins also known as gallectins, bind to gallactose. The collectins have a collagen like tail, such as mannose binding protein.

Other CAMs include selectin ligands. The sugars that the selectins bind to are mainly sialylated and fucosylated tetrasaccharide antigens called Lewis sugars. Examples include Le$^x$ (LPE), 3-sulpho Le$^x$ (E) and 3-sialo Le$^x$ (L), and sulphated tyrosines (of PSGL) (P). The N-linked sugars are usually bi- or teraantennary. The conformation and linkage of the sugars are very important for the overall shape (e.g., a 1-3 and a 1-4 linkage can cause the sugars to look completely different).

Integrins are a large family of heterodimeric transmembrane glycoproteins that attach cells to extracellular matrix proteins. Integrins contain large ($\alpha$) and small ($\beta$) subunits of sizes 120-170 kDa and 90-100 kDa, respectively. For tight adhesion to occur between activated endothelial cells and leukocytes, $\beta2$-containing integrins on the surfaces of leukocytes also must be activated by chemokines or other local activation signals such as platelet-activating factor (PAF). Activated integrins on leukocytes then bind to each of two distinct IgCAMs on the surface of endothelial cells: ICAM-2, which is expressed constitutively, and ICAM-1. ICAM-1, whose synthesis along with that of E-selectin and P-selectin is induced by activation, does not usually contribute substantially to leukocyte endothelial cell adhesion immediately after activated, but rather participates at later times in cases of chronic inflammation. The resulting tight adhesion mediated by the $Ca^{2+}$ independent integrins-ICAM interactions leads to the cessation of rolling and to the spreading of leukocytes on the surface of the endothelium. The adhered cells then move between adjacent endothelial cells and into the underlying tissue. Integrins contain binding sites for divalent cations $Mg^{2+}$ and $Ca^{2+}$, which are necessary for their adhesive function. Mammalian integrins form several subfamilies sharing common $\beta$ subunits that associate with different $\alpha$ subunits. Integrin ligands include NCAM and Fibronectin. These ligands have Ig domains and can be anchored to membrane by GPI anchor or TM helix. Other CAMs include clustered determinants, known as the CD molecules, which mostly have Ig domains. Other CAMs include pMHC and TCR; proteoglycans, having long unbranched glycans; and growth factors (FGF, EGF and NGF), which bind to haparan sulphate to be recognized by receptor.

The activated lymphocyte has many glycoproteins and cell adhesion molecules on its surface, eg TCR, CD43 (hyperglycosylated spacer) and ICAM. These molecules are important for the recognition of foreign antigens, activation of APCs and toxic effects on other cells. The lymphocytes interact with the APC via specific interactions (TCR) and non-specific interactions (CD2—LFA3 and ICAM-1—LFA1).

Upon infection of tissue, cytokines are secreted that make the endothelial cells express E- and P-selectins on their surface. These will interact with glycoproteins on the surface on the leukocytes in the blood stream, making the cells slow down by a rolling movement. The target of P-selectin is PSGL on the surface of the leukocyte, having a heavily O- and N-linked glycoprotein tyrosine-sulphate content. The target of E-selectin is unknown. The leukocyte also has a selectin on its surface (L). The targets of this are CD34, MAdCAM-1 (both with IgSF domains and lots of N- and O-linked glycosylation) and GlyCAM-1 (soluble inhibitor of the mucin family). When the leukocyte is stopped it will exrtavasate aided by chemoattractants (such as RANTES) and integrin adhesion to fibronectin of epithelia.

Lymphocytes are capable of a remarkable level of recirculation, continuously moving through the blood and lymph to various lymphoid organs. About 40-50% of the lymphocytes will be recruited to the spleen, about 38-48% will be recruited to various peripheral lymph nodes and the remainder will be recruited to various mucosal-associated lymphoid tissues (MALT) or SALT (skin associated lymphoid tissues). In order for recirculating lymphocytes to enter various lymphoid organs or inflammatory-tissue spaces, the lymphocytes must adhere to a pass between the endothelial cells lining the walls of blood vessels by extravasation. Vascular endothelial cells possess cell adhesion molecules on their surface. Some of these are expressed constitutively and others are inducible (expressed primarily in response to certain cytokines produced during an inflammatory response).

Selectins are membrane glycoproteins with a distal lectin-like domain which enables the protein to bind to specific carbohydrate moieties. L-selectin is expressed on all leukocytes while E- and P-selectin are expressed on vascular endothelial cells. Cadherins (or mucins) are serine- and threonine-rich proteins that are heavily glycosylated. They present sialyated carbohydrate ligands to selectins. For instance, L selectin on leukocytes recognizes sialylated carbohydrates on two mucin-like molecules (CD34 and GlyCAM-1) expressed on certain endothelial cells of lymph nodes. PSGL-1 on neutrophils interacts with E and P-selectin on inflamed endothelium. Other CAMs include the category known as Integrins, which generally have a $\alpha\beta$-heterodimers structure. Integrins are integral membrane proteins expressed by leukocytes which facilitate adherence to the vascular endothelium. Different integrins, including LFA-1, are expressed by different populations of leukocytes, allowing these cells to bind to different CAMs belonging to the Ig family expressed along the vascular endothelium. LAD (leukocyte adhesion deficiency) is an autosomal recessive disease characterized by recurrent bacterial infections and impaired wound healing. Abnormal synthesis of the B chain in integrins characterize the LAD disorder. As a result of the abnormal synthesis, leukocytes cannot extravasate. The Ig superfamily of CAMs are proteins which contain at least one Ig-domain such as ICAM-1,2,3 and VCAM on vascular endothelial cells. The protein MAdCAM has both Ig and mucine-like domains expressed by mucosal endothelial cells. It directs lymphocytes into the mucosa. It binds to integrins via its immunoglobulin-like domain and to selectins via its mucin-like domain.

During an inflammatory response cytokines and other chemicals act on local blood vessels (dilation and increased permeability) to show an increased expression of CAMs. When this happens the vascular endothelium is said to be inflamed or activated. Neutrophils are among the first cells to bind and extravasate. This process is similar for monocytes but better studied for neutrophils. Extrasvastion of neutrophils includes: rolling chemoattractant activating stimulus arrest and adhesion and transendothelial migration rolling. Initially low affinity selectin-carbohydrate interaction is observed during inflammation. E and P selectins expressed in higher levels on vascular endothelial cells bind to mucin-like cell adhesion molecules on the neutrophil membrane. As the neutrophil rolls, it is activated by various chemoattractants that are localized on the endothelial cell surface or secreted locally by cells involved in the inflammatory process. Chemoattractive cytokines (or chemokines) include IL-8, macrophage inflammatory protein (MIP), PAF, and C5a. Adhesion binding to chemokines triggers G protein activated signal transduction pathway, which induces a conformational change in integrins, increasing their affinity for Ig superfamily CAMs on the endothelium. Extravasation directed migration of the neutrophil through interendothelial junctions has not been well characterized.

Antigen specific T cells are known to disappear from the circulation in less than 48 hours. Recruitment of T cells occurs especially at locations called High Endothelial Venules (HEVs), which are plump, cuboidal cells present in all secondary lymphoid sites except the spleen. Appearance or expression of HEVs dependent upon antigen stimulation. These HEVs express on their surface special CAMs. Antigen stimulation results in an increased expression of these CAMs thereby facilitating extravasation. Germ-free animals do not have HEVs. Re-circulating lymphocytes, monocytes, and granulocytes bear adhesion-molecule receptors for: CAMs of the selectin family, the mucin family (GlyCAM-1 and CD34), and the Ig superfamily (ICAM-1-3, VCAM-1, and MAdCAM-1). When distributed in a tissue-specific way these molecules are termed: vascular adressins. The corresponding receptors on endothelial cells have come to be called homing receptors. The homing receptors recruit different subsets of lymphocytes, which migrate differentially into different tissues based on the expression of the homing receptors and also due to chemokine secretion patterns and differential responses. For example, MIP (macrophage inhibitory protein) preferentially attracts naive T cells. Monocyte chemoattractant protein (MCP) and RANTES preferentially attract memory T cells. Naive lymphocytes initial attachment to HEVs are generally mediated by binding of homing receptor L-selectin to vascular adressins such as GlycCAM-1 and CD34 on HEVs. If the lymphocytes encounter antigens within the node, they become activated and enlarge into lymphoblasts and are retained for at least 48 hours. The lymphoblasts experience rapid proliferation and differentiation to effector and memory cells which then leave the node. Effector and Memory Lymphocytes tend to home to regions of infection. Memory lymphocytes are attracted to the type of tissue where they originally encountered the antigen. These cells express high levels of certain homing receptors, this allows tissue-specific homing behavior.

Table 1 below summarizes the circulating cellular and endothelial interactions of several embodiments of the present invention.

Figure 2:
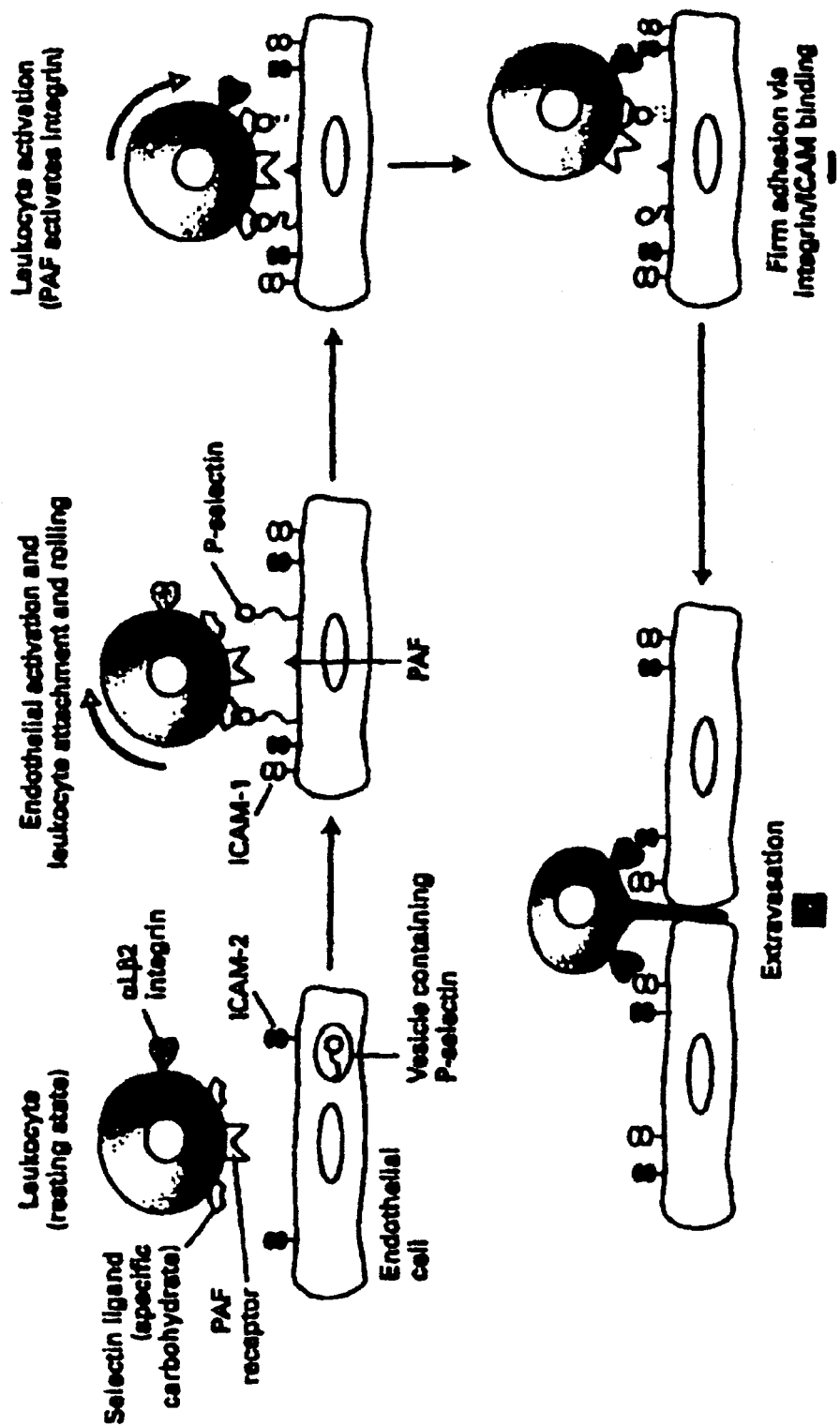
FIG. 2 is a schematic drawing of the sequence of cell-cell interactions leading to tight binding of leukocytes to activated endothelial cell and subsequent extravasation.

The leukocyte cascade sequence is illustrated at FIG. 2. In the absence of inflammation or infection, leukocytes and endothelial cells lining blood vessels are in a resting state. Inflammatory signals released in areas of inflammation or infection activate resting endothelial cells to move vesicle-sequestered selectins to the cell surface. The exposed selectins mediate loose binding of leukocytes by interacting with carbohydrate ligands on leukocytes. Activation of the endothelium also causes synthesis of platelet-activating

| Endothelial component | Cell component | Glycosylation |
| --- | --- | --- |
| L-Selectin (cd62L) | Counter receptors on leukocytes PSGL-1 (cd162) MadCAM-1 CD34 GlyCAM-1 | Counter receptors O-linked glycosylation |
| P Selectin | PSGL-1 CD-24 | Counter receptors O-linked glycosylation |
| E Selectin | PSGL-1 (hypothesized) ESL-1 (hypothesized) | Counter receptors O-linked glycosylation |
| Beta Integrins ICAM-1,2 (Intracellular) PECAM-1 (Platelet, endoth) VCAM-1 (Vascular) | LFA-1, MAC-1 | Beta integrins glycosylated |
| Neurothelin (cd147) | | Neurothelin glycosylated |
| CD151 (Transmembrane 4 superfamily protein: PETA-3, SFA-1) | | Glycosylated |
| BST-1 (Bone marrow stromal cell antigen-1) CD18, 29, 49 VLA-4 LPAM-2 | | Glycosylated |
| I-selectin | CD34: FLT-3, FLT-3Ligand | CD34 - Glycosylated |

Factor (PAF) and ICAM-1, both expressed on the cell surface. PAF and other usually secreted activators, including chemokines, then induce changes in the shapes of the leukocytes and activation of leukocyte integrins such as αβ2, which is expressed by T lymphocytes. The subsequent tight binding between activated integrins on leukocytes and CAMs on the endothelium (e.g., ICAM-2 and ICAM-1) results in firm adhesion and subsequent movement (extravasation) into the underlying tissue.

The selective adhesion of leukocytes to the endothelium near sites of infection or inflammation thus depends on the sequential appearance and activation of several different CAMs on the surfaces of interacting cells. It has been found that several CAMs and associated circulating leukocytes express carbohydrate chains comprising chondroitin sulfate proteoglycans (CSPG).

CSPGs are a family of proteoglycans composed of a core protein and covalently linked sulfated glycosaminoglycans. Each proteoglycan is determined by the glycosaminoglycan side chains. For CSPGs these side chains are made up of approximately 40 to 100 sulfated disaccharides composed of chondroitin 4, 6 and dermatan sulfates. The protein component of the CSPG is ribosomally synthesized and the glycosylation occurs in the endoplasmic reticulum and Golgi apparatus. The sugar chains are then sulfated at the 4 or 6 positions by several glycosaminoglycan sulfotransferases.

Disruption of the glycosylation interaction between CAMs and associated receptors in the extravasation cascade through targeting of carbohydrate chains. A disruption of cell-cell adhesion thus disrupts extravasation of leukocytes into tissue cells. It has been found that the use of enzymes directed against the CSPG carbohydrate chains allows for regulation and modification of extravasation processes. The enzyme may be directed against the CSPG carbohydrate chains of ligands expressed on circulating leukocytes. Thus, the leukocytes are not able to adhere to the integrins, mucins, or selectins localized on the blood-facing surface of endothelial cells. As described herein, the ligands for endothelial cell surface CAMs include the ligands for adhesion to the selectin family, the mucin family and the integrin family. Any ligand expressed on leukocytes containing CSPG carbohydrate chains may be targeted in the several treatments and methods of the present invention.

As used herein, a compound directed against CSPG is a molecule that can degrade CSPG chains, cleave CSPG, bind to CSPG, or inhibit other compounds or cells from adhering to CSPG. A non-limiting example of compounds directed against CSPG includes the chondroitinase enzymes. The administration of compounds directed against CSPG may be used to control extravasation of leukocytes, thus modification of the immune response is possible.

Thus the use of enzymes directed against CSPG may be used to prevent, treat and alleviate symptoms of inflammation and inflammatory states. The enzyme may also prevent, treat and alleviate symptoms of chronic inflammatory diseases and central nervous system disorders. The enzyme may be used to treat inflammation associated with pain, injection and diseased states. The enzyme may be used to prevent tissue damage that is associated with inflammatory processes. Several conditions may benefit from controlled immune response. The many types of allergies and many of the autoimmune diseases are examples of inflammation in response to what should have been a harmless, or at least noninfectious, agent. Some examples of chronic inflammatory diseases include Asthma, Rheumatoid Arthritis (RA), Multiple Sclerosis (MS), Systemic Lupus Erythematosus (SLE), and Chronic Obstructive Pulmonary Disease (COPD). The use of enzymes directed against CSPG may also be used to regulate the inflammatory state associated with one or more disease selected from the group consisting of central nervous system disorders, central nervous system diseases, spinal cord injury, and cardiovascular diseases.

Inflammatory diseases, autoimmune diseases, and diseases with an inflammatory component may also include Multiple Sclerosis, Meningitis, Encephalitis, Rheumatoid arthritis, Osteo arthritis, Lupus, Wegener's granulomatosis, Inflammatory bowel disease: Crohn's colitis, ulcerative colitis, Asthma, Chlamydia infections, Syphilis, Thyroiditis, Temporal arteritis, Polymyalgia rheumatica, Ankylosing spondylitis, Psoriasis, Vasculitiditis such as: temporal arteritis, Takayasu arteritis, syphilitic aortitis, infectious aneurisms, atherosclerotic aneurisms, inflammatory abdominal aortic aneurysms, polyarteritis nodosa, Kawasaki disease, Churg-Strauss, hypersensitivity vasculitis, Buerger's disease, mesenteric inflammatory veno-occlusive disease, phlebitis, thrombophlebitis, Churg-Strauss, primary angiitis of the CNS, drug induced vasculitis, any secondary arteritis or venulitis, Gout, Pseudogout, Sarcoidosis, Sjogren's Syndrome, Myelitis, Salpingitis of any etiology, Uveitis, Pelvic Inflammatory Disease, Glomerulonephritis of any etiology, Goodpasture's syndrome, Pericarditis, Myocarditis, Endocarditis, and Pancreatitis.

Suitable enzymes that are directed against CSPGs include chondroitinase ABC type I, chondroitinase ABC Type II, chondroitinase AC and Chondroitinase B or mammalian enzymes with chondroitinase-like activity such as hyaluronidase 1, hyaluronidase 2, hyaluronidase 3, hyaluronidase 4, cathepsins, and ADAMTs, fragments thereof or mixtures thereof.

Chondroitinases are enzymes of bacterial origin that act on chondroitin sulfate, a component of the proteoglycans that are expressed in various CAMs and receptors associated with inflammatory response. Examples of chondroitinase enzymes are chondroitinase ABC, which may be produced by the bacterium *Proteus vulgaris* (*P. vulgaris*), and chondroitinase AC, which may be produced by *A. aurescens*. Chondroitinases ABC and AC function by degrading polysaccharide side chains in protein-polysaccharide complexes, without degrading the protein core.

It has now been found that the CSPG-degrading enzymes such as chondroitinase ABCTypeI, chondroitinase ABC-TypeII, chondroitinase AC, chondroitinase B or mammalian enzymes with chondroitinase-like activity such as Hyal 1, Hyal 2, Hyal 3, and Hyal 4 are useful in controlling and/or inhibiting the effects of chondroitin sulfates and in developing therapeutics for the regulation, treatment and prevention of inflammation associated with various disease states.

Yarnagata et al. (J. Biol. Chem. 243:1523-1535, 1968) describe the purification of the chondroitinase ABC from extracts of *P. vulgaris*. This enzyme selectively degrades the glycosaminoglycans chondroitin-4-sulfate, dermatan sulfate, and chondroitin-6-sulfate (also referred to respectively as chondroitin sulfates A, B, and C which are side chains of proteoglycans) at pH 8 at higher rates than it degrades chondroitin or hyaluronic acid. *P. vulgaris* chondroitinase I migrates with an apparent molecular mass of about 110 kDa when resolved by SDS-PAGE. The products of the degradation are high molecular weight unsaturated oligosaccharides and an unsaturated disaccharide. However, chondroitinase ABC does not act on keratosulfate, heparin or heparitin sulfate.

Another chondroitinase, chondroitinase II, has also been isolated and purified from *P. vulgaris*, Chondroitinase II is a polypeptide of 990 amino acids with an apparent molecular mass by SDS-PAGE of about 112 kDa. Its molecular mass as determined by electrospray and laser desorption mass spectrometry is 111,772.+−0.27 and 111,725.+−0.20 daltons, respectively. Chondroitinase II has an isoelectric point of 8.4-8.45. Its enzymatic activity is distinct from, but complementary to, that of chondroitinase I. Chondroitinase I endolytically cleaves proteoglycans to produce end-product disaccharides, as well as at least two other products which are thought to be tetrasaccharides, Chondroitinase II digests at least one of these tetrasaccharide products of chondroitinase I digestion of proteoglycan.

Chondroitinase AC and chondroitinase B are chondroitin lyase enzymes, which may be derived from various sources. Any chondroitinase AC or B may be used in the present method embodiments including, but not limited to chondroitinase AC (derived from *Flavobacterium heparinum*; T. Yamagata, H. Saito, O. Habuchi, S. Suzuki, J. Biol. Chem., 243, 1523 (1968)); chondroitinase AC II (derived for *Arthobacter aurescens*; K. Hiyama, S. Okada, J. Biol. Chem., 250, 1824 (1975), K. Hiyama, S. Okada, J. Biochem. (Tokyo), 80, 1201 (1976)); chondroitinase AC III (derived from *Flavobacterium* sp. Hp102; H. Miyazono, H. Kikuchi, K. Yoshida, K. Morikawa, K. Tokuyasu, Seikagaku, 61, 1023 (1989)); chondroitinase B (derived from Flavobacterium heparinum; Y. M. Michelaaci, C. P. Dietrich, Biochem. Biophys. Res. Commun., 56, 973 (1974), V. M. Michelaaci, C. P. Dietrich, Biochem. J., 151, 121 (1975), K. Maeyama, A. Tawada, A. Ueno, K. Yoshida, Seikagaku, 57, 1189 (1985)); and chondroitinase B (derived from *Flavobacterium* sp. Hp102; H. Miyazono, H. Kikuchi, K. Yoshida, K. Morikawa, K. Tokuyasu, Seikagaku, 61, 1023 (1989)). Suitable chondroitinase AC and chondroitinase B are commercially available from Seikagaku America, Falmouth, Mass., USA. Additionally, the enzymes may be produced by the methods disclosed in U.S. Pat. No. 6,093,563 by Bennett et al., the disclosure of which is incorporated herein. Chondroitinase I and chondroitinase II are exo- and endo-lyases respectively which cleave both chondroitin and dermatan sulfates (Hamei et al 1997). Mammalian enzymes with chondroitinase-like activity have been identified. For example, certain hyaluronidases such as Hyal 1, Hyal 2, Hyal 3, and Hyal 4 also degrade CSPGs and can be used in the present invention.

Hyaluronidase is an enzyme that catalyzes the breakdown of hyaluronic acid in the body, thereby increasing tissue permeability to fluids. It is also known as a spreading factor. The hyaluronidase (endo-N-acetylhexosaminidase) enzyme acts on not only hyaluronan but also chondroitin, chondroitin 4-sulfate and chondroitin 6-sulfate. Besides the hydrolytic reaction, hyaluronidase is also known to catalyze the reverse reaction, transglycosylation.

Hyaluronidase may be purified from mammalian testicular and spleen tissue (common sources are bovine and ovine testes), venom from bees and snakes, and many bacteria. The enzyme has a molecular weight of 55,000 daltons. The function of this enzyme is to catalyze the depolymerization of mucopolysaccharides, hyaluronic acid, and the chondroitin sulfates A and C. This enzyme is commonly used in medical practice to encourage intradermal drug absorption in patients and in increasing the efficiency of local anesthetics.

An enzyme that is directed against both hyaluronic acid and chondoritinase sulfate is also suitable in the several method embodiments of the present invention. *Treponema denticola, Treponema vincentii* and *Treponema socranskii* produce an enzyme that hydrolyses hyaluronic acid and chondroitin sulfate. The secreted enzyme is specifically inhibited by gold sodium thiomalate and anti-bee-venom antibodies. The affinity-purified extracellular enzyme of *T. denticola* contains a single molecular species with a molecular mass of 59 kDa. Since it hydrolyses both HA and CS, this enzyme is termed a hyaluronoglucosaminidase (HGase).

Another embodiment of the present invention is a method of treating inflammation in a patient comprising extracting circulating cells from a patient, subjecting the cells to an enzyme that cleaves the expressed chondroitin sulfate proteoglycan ex vivo to modify the cells, and administering the modified blood cells into the patient. Therefore, the use of enzymes directed against CSPG described herein may also be directed to ex vivo treatments.

Extraction of cells may be accomplished by a variety of methods including, but not limited to, intravenous blood withdrawal, transfusion, dialysis, bypass, organ transplant and other similar methods that result in removal of cells from the body. Administration of the cells may be accomplished by the same methods used to extract the cells, including, but not limited to, intravenous blood withdrawal, transfusion, dialysis, bypass, organ transplant and the like.

A circulating leukocyte with ligands expressed on its surface containing carbohydrate chains may be extracted from a patient and modified ex vivo by the presently described enzymes. Extraction may be accomplished by blood draw, transfusion, dialysis, bypass, or organ transplant. As described, the enzymes would modify the carbohydrate chains, specifically any compound directed against CSPG would be suitable to modify the extracted leukocytes. Once modified, the leukocytes may be reintroduced into a patient's blood stream. Modified leukocytes will be incapable of adhering to endothelial expressed selectins, mucins, and integrins. Timing of such extraction and reintroduction into the bloodstream may be optimized by observing the inflammatory response and the appearance of leukocytes in the blood stream, once said cells are signaled to specific sites of injury or infection. As a result, extravasation of leukocytes into tissue may be regulated, prevented, reduced, or controlled. Such regulation may be used in methods and treatments as directed to control and treat inflammatory response and diseases with an inflammatory component.

Enzyme activity can be stabilized by the addition of excipients or by lyophilization. Stabilizers include carbohydrates, amino acids, fatty acids, and surfactants and are known to those skilled in the art. Examples include carbohydrate such as sucrose, lactose, mannitol, and dextran, proteins such as albumin and protamine, amino acids such as arginine, glycine, and threonine, surfactants such as TWEEN® and PLURONIC®, salts such as calcium chloride and sodium phosphate, and lipids such as fatty acids, phospholipids, and bile salts. The stabilizers are generally added to the protein in a ration of 1:10 to 4:1, carbohydrate to protein, amino acids to protein, protein stabilizer to protein, and salts to protein; 1:1000 to 1:20, surfactant to protein; and 1:20 to 4:1, lipids to protein. Other stabilizers include high concentrations of ammonium sulfate, sodium acetate or sodium sulfate, based on comparative studies with heparinase activity. The stabilizing agents, such as the ammonium sulfate or other similar salt, are added to the enzyme in a ratio of 0.1 to 4.0 mg ammonium sulfate/IU enzyme.

Enzymes may be administered intravenously, through local or systemic injection. Systemic administration is preferable for greater control of application. Other administrations include subcutaneous, transdermal, transmucosal, and enteric coating formulations. The enzymes, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing agents, preservants, anesthetics and the like. Specifically pharmaceutical carrier that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds.

A pharmaceutical carrier may also be used. Suitable carriers include polyethylene glycol and/or sucrose, polyoxyethylene sorbitan fatty acid esters, polyethylene sorbitan monooleate, and the like, and combinations thereof.

The dose will also vary depending on the manner of administration, the particular symptoms of the patient being treated, the overall health, condition, size, and age of the patient, and the judgment of the prescribing physician. Dosage levels of the therapeutic CSPG enzymes for human subjects range between about 0.001 mg per kg and about 100 mg per kg per patient per treatment.

The treatment regimens of the present invention may be carried out by a means of administering chondroitinase $ABC_{TypeI}$, chondroitinase $ABC_{TypeII}$, chondroitinase AC and chondroitinase B or mammalian enzymes with chondroitinase-like activity such as Hyal1, Hyal2, Hyal3, and Hyal4 in vivo or ex vivo. In vivo administration may include systemic intravenous administration to the area of inflammation. The mode of administration, the timing of administration and the dosage are carried out such that the inflammation is prevented or reduced by modifying extravasation of cells. The treatments of the present disclosure deliver an effective amount of chondroitinase $ABC_{TypeI}$, chondroitinase $ABC_{TypeII}$, chondroitinase AC and chondroitinase B or mammalian enzymes with chondroitinase-like activity such as Hyal 1, Hyal 2, Hyal 3, and Hyal 4, or fragments or combinations thereof to the injured site. The term "effective amount" means an amount sufficient to degrade the CSPGs or an amount sufficient to modify extravasation of cells. The effective amount of chondroitinase can be administered in a single dose or a plurality of dosages.

Although it is to be understood that the dosage may be administered at any time, in one embodiment, the dosage is administered within hours of the signaling of inflammatory response, or as soon as is feasible. In another embodiment, the dosage is administered to a mammal in one, two or a plurality of dosages; such dosages would be dependant on the severity of the injury and the amount of CSPGs present. Where a plurality of dosages is administered, they may be delivered on a daily, weekly, or bi-weekly basis. The delivery of the dosages may be by means of catheter or syringe. Alternatively, the treatment can be administered during surgery to allow direct application to the site of inflammation or injury. Subject to the judgment of the physician, a typical therapeutic treatment includes a series of doses, which are usually administered concurrent with the monitoring of clinical endpoints.

The therapeutic CSPG enzymatic agents may be administered by methods known in the art, such as by bolus injection, intravenous delivery, continuous infusion, or sustained release formulation, such as implants and the like.

Formulations suitable for injection are found in *Remington's Pharmaceutical Sciences*, Mack Publishing Company, Philadelphia, Pa., 17$^{th}$ ed. (1985). Such formulations include antibacterial preservatives, buffers, solubilizers, antioxidants, and other pharmaceutical adjuncts. Such formulations must be sterile and non-pyrogenic, and generally will include purified therapeutic porcine B7-1 agents in conjunction with a pharmaceutically effective carrier, such as saline, buffered (e.g., phosphate buffered saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

EXAMPLES

Example 1

Toxicity Studies. Female Long Evans rats from Charles River Laboratories, weighing approximately 210 grams were housed in the Acorda Animal Care Facility for 5 days prior to injection to ensure health and weight stability. Rats were anesthetized with isoflurane and injected i.v. via tail veins with chondroitinase ABC I (Seikagaku; Cat number 100332, lot number E02201). Animals were injected with either 0, 0.2, 0.775 or 7.775 mg/kg with solutions containing 0, 0.2, 0.775 and 7.775 mg/ml, respectively in Hank's balanced salt solution.

Additionally, toxicity studies were conducted for Intrathecal (IT) catheter administration. Intrathecal catheters were placed in 16 normal, un-injured female rats at about the T13/L1 vertebral junction for delivery of chondroitinase. Catheters were fed rostrally to rest at the T9/T10 level to simulate previous chondroitinase studies. Twenty-four hours after intrathecal catheter placement animals were dosed with 0, 0.06, 0.6 or 6.0 Units of Acorda chondroitinase ABCI (100 Units/milligram) in 20 microliters of artificial cerebrospinal fluid over a 20 minute period.

Animals were observed for 24 hours or 7 days and their weights and temperatures were followed. Animals were monitored for pain and distress and body weights were acquired daily. No overt reactions were observed during or immediately after chondroitinase ABCI dosing. No swelling, inflammation, bruising or necrosis was noted at the injection site for the IV experiment. No changes in body temperature were observed in animals treated via the IT route. No alterations in feeding, grooming or vocalizations were noted. Animals were assessed for motor behavior in an open pool. No abnormalities were noted by the animal care staff or behavioral specialists. Animals displayed no signs of joint tenderness or swelling. There were no significant differences in weight change between the treatment groups. The results demonstrate that chondroitinase ABCI treatment is not associated with acute toxicity using IV doses. Additionally, Chondroitinase appears safe in single intrathecal (I.T.) doses.

What has been described and illustrated herein are embodiments of the invention along with some of their variations. The terms, descriptions and figures used herein are set forth by way of illustration only and are not meant as limitations. Those skilled in the art will recognize that many variations are possible within the spirit and scope of the invention, which is intended to be defined by the following claims and their equivalents in which all terms are meant in their broadest reasonable sense unless otherwise indicated.

What is claimed:

1. A method of treating inflammation in a patient comprising:
   extracting cells circulating in the blood stream of a patient;
   subjecting the cells to an enzyme that cleaves chondroitin sulfate proteoglycan ex vivo to modify the cells, wherein the cells are selected from the group consisting of neutrophils, eosinophils, basophils, lymphocytes, B-cells, T-cells, monocytes, and macrophages; and
   administering the modified cells to the patient.

2. The method of claim 1, wherein the enzyme is selected from the group consisting of chondroitinase ABC Type I, chondroitinase ABC Type II, chondroitinase AC, chondroitinase B, Hyaluronidase 1, Hyaluronidase 2, Hyaluronidase 3, Hyaluronidase 4, and hyaluronoglucosaminidase.

3. The method of claim 1, wherein the enzyme is directed against integrins containing chondroitin sulfate proteoglycans expressed on the surface of the cells circulating in the blood stream.

4. The method of claim 1, wherein the cells are extracted from the blood stream of the patient after activation of the immune response of the patient.

5. The method of claim 1, wherein the cells are extracted from the blood stream of a patient prior to activation of the immune response of the patient, and the modified cells are administered to the patient after the activation of the immune response.

\* \* \* \* \*